(12) United States Patent
Yamada et al.

(10) Patent No.: US 12,371,323 B2
(45) Date of Patent: Jul. 29, 2025

(54) ZIRCONIUM PHOSPHATE PARTICLES, BASIC GAS DEODORANT USING THE SAME, AND PRODUCTION METHOD THEREOF

(71) Applicant: TOAGOSEI CO., LTD., Tokyo (JP)

(72) Inventors: Yoshinao Yamada, Nagoya (JP); Tatsuya Sogou, Nagoya (JP); Shinya Kumagai, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 410 days.

(21) Appl. No.: 17/910,097

(22) PCT Filed: Mar. 4, 2021

(86) PCT No.: PCT/JP2021/008464
§ 371 (c)(1),
(2) Date: Sep. 8, 2022

(87) PCT Pub. No.: WO2021/182299
PCT Pub. Date: Sep. 16, 2021

(65) Prior Publication Data
US 2023/0115027 A1    Apr. 13, 2023

(30) Foreign Application Priority Data
Mar. 13, 2020 (JP) .................. 2020-044208

(51) Int. Cl.
| | |
|---|---|
| *C01B 25/37* | (2006.01) |
| *A61L 9/01* | (2006.01) |
| *C08L 75/06* | (2006.01) |
| *D06M 11/71* | (2006.01) |

(52) U.S. Cl.
CPC .............. *C01B 25/372* (2013.01); *A61L 9/01* (2013.01); *C08L 75/06* (2013.01); *D06M 11/71* (2013.01)

(58) Field of Classification Search
None
See application file for complete search history.

(56) References Cited

U.S. PATENT DOCUMENTS

2009/0272293 A1 * 11/2009 Yasuharu

FOREIGN PATENT DOCUMENTS

| CN | 110591294 A | 12/2019 |
|---|---|---|
| JP | 3896327 B | 3/2007 |
| JP | 2012-224517 A | 11/2012 |
| JP | 2012-224518 A | 11/2012 |
| JP | 2012-233203 A | 11/2012 |
| JP | 2012224517 * | 11/2012 |
| JP | 2018-178313 A | 11/2018 |
| JP | 2018178313 * | 11/2018 |
| WO | WO 2008/053694 A1 | 5/2008 |
| WO | WO 2012/050156 A1 | 4/2012 |

OTHER PUBLICATIONS

PCT Search Report, May 18, 2021, 2 pages.
Chinese Office Action (w/ English translation) for corresponding Application No. 202180020596.X, dated Nov. 16, 2023, 16 pages.

* cited by examiner

*Primary Examiner* — Robert A Wax
*Assistant Examiner* — Kimberly Barber
(74) *Attorney, Agent, or Firm* — Dority & Manning, P.A.

(57) ABSTRACT

Provided are zirconium phosphate particles, obtained by bringing α-zirconium phosphate particles into contact with a basic liquid having a pH of 9 or higher and then further bringing the particles into contact with an acidic liquid having a pH of 6 or lower, or zirconium phosphate particles, in which, after leaving for 10 minutes from putting 10 mg of zirconium phosphate particles and 3 L of air that contains 1,000 ppm of an ammonia gas into a test bag at normal temperature and normal pressure, an ammonia gas reduction rate within the test bag that contains the zirconium phosphate particles is 50% or more.

20 Claims, No Drawings

ZIRCONIUM PHOSPHATE PARTICLES, BASIC GAS DEODORANT USING THE SAME, AND PRODUCTION METHOD THEREOF

CROSS-REFERENCE TO RELATED APPLICATIONS

The present application is related and has right of priority to JP 2020-044208, which was filed on Mar. 13, 2020 in the Japanese Patent Office, and is a U.S. national phase entry of PCT/JP2021/008464, which was filed on Mar. 4, 2021, both of which are incorporated by reference in their entireties for all purposes.

TECHNICAL FIELD

The present invention relates to zirconium phosphate particles as well as a fine particle basic gas deodorant, a deodorant for fibers, a composition for deodorizing processing, a deodorizing resin composition and deodorizing fibers, each using the particles, and belongs to the technical field of adsorbent, the technical field of deodorant, and the technical field of resin and fibers.

BACKGROUND ART in recent years, with the demand for safer and more comfortable living environment, "deodorizing products" for the purpose of adsorbing and deodorizing harmful gases or odorous gases have become available, such as deodorizing sheets, deodorizing curtains, deodorizing filters, as well as clothes and bedclothes that have deodorizing function with respect to sweat odor, aging odor, fatigue odor, or the like.

As typical gases to be adsorbed and gases to be deodorized, acid gases such as acetic acid, basic gases such as ammonia, sulfur-based gases such as methyl mercaptan, aldehyde-based gases such as formaldehyde, and ketone-based gases such as acetone are known, and deodorants or deodorizing products that are suitable for each gas have been developed. In recent years, attention has been drawn to basic gas adsorbents or basic gas deodorizing products that are capable of adsorbing a basic gas such as ammonia, which is a causative substance of sweat odor or fatigue odor. For example, deodorizing products have been developed in which an inorganic solid acid such as zirconium phosphate is used as a basic gas adsorbent, and is supported on or kneaded into fibers or the like.

For example, in order to deodorize sweat odor or fatigue odor, development of clothes using deodorizing fibers has been studied and, for such purposes, there is growing demand for deodorizing a basic gas such as ammonia, which is a causative substance thereof, as quickly as possible.

Japanese Patent Publication No. 3,896,327 discloses a filter for adsorbing an ammonia gas, in which 0.5 to 4 parts by weight of α-type zirconium phosphate are supported on 1 parts by weight of fibrillated fibers, and a propylene glycol monomethyl etheracetate decomposition rate is less than 4%.

Japanese Patent Application Laid-Open (JP-A) No. 2018-178313 discloses a deodorant for fibers, the deodorant including α-zirconium phosphate, in which, as particle size, a median diameter is from 0.2 to 0.7 μm, a maximum particle size is 5.0 μm or less, and a $D_{10}$ diameter is 0.1 μm or more.

SUMMARY OF INVENTION

Technical Problem

However, regarding the filter for adsorbing an ammonia gas disclosed in Japanese Patent Publication No. 3,896,327, a flat plate-shaped filter for adsorption is produced by blending 2.34 parts by weight of α-type zirconium phosphate having an average diameter of 0.9 μm with respect to 1.0 parts by weight of a fibril compound of aramid fibers and, in order to achieve sufficient high-speed deodorizing performance, there was a need to use a large amount of α-type zirconium phosphate with respect to fibers. Further, it was not practical to apply this technique to deodorizing fibers or deodorizing clothes.

Further, although the deodorizing fibers described in JP-A No. 2018-178313 improves spinnability and deodorizing property by controlling the particle size of the deodorant that is kneaded into the fibers to a certain value or less, there was no description or suggestion with regard to the problem on high-speed deodorizing property and the solution thereof.

According to one embodiment of the present invention, it is an object to provide zirconium phosphate particles that have high deodorizing performance with respect to a basic gas such as ammonia and trimethylamine and are particularly excellent in deodorizing rate with respect to ammonia, as well as a deodorant, a composition for deodorizing processing, a deodorizing resin composition and deodorizing fibers, each using the particles, and a production method thereof.

Solution to Problem

The present invention includes the following aspects [1] to [21].

[1] Zirconium phosphate particles, obtained by bringing α-zirconium phosphate particles into contact with a basic liquid having a pH of 9 or higher and then further bringing the particles into contact with an acidic liquid having a pH of 6 or lower.

[2] The zirconium phosphate particles according to [1], in which the basic liquid includes at least one of an alkali metal or an alkaline earth metal.

[3] Zirconium phosphate particles, in which, after leaving for 10 minutes from putting 10 mg of zirconium phosphate particles and 3 L of air that contains 1,000 ppm of an ammonia gas into a test bag at normal temperature and normal pressure, an ammonia gas reduction rate (X; unit %) represented by Formula (1) below within the test bag that contains the zirconium phosphate particles is 50% or more:

$$X = \{(A_0 - A_1)/A_0\} \times 100 \qquad \text{Formula (1):}$$

in which, in Formula (1), $A_0$ means an ammonia gas concentration in the test bag that does not contain zirconium phosphate particles, and $A_1$ means an ammonia gas concentration in the test bag that contains the zirconium phosphate particles.

[4] The zirconium phosphate particles according to any one of [1] to [3], in which a median diameter of primary particles is from 0.1 to 10 μm.

[5] The zirconium phosphate particles according to any one of [1] to [4], in which a dry reduction rate (Y; unit % by weight) represented by Formula (2) below after heating at 150° C. for 2 hours is 5.0% by weight or less:

$$Y = \{(B_0 - B_1)/B_0\} \times 100 \qquad \text{Formula (2):}$$

in which, in Formula (2), $B_0$ means a weight of the zirconium phosphate particles before heating, and $B_1$ means a weight of the zirconium phosphate particles after heating,

[6] A basic gas deodorant, including the zirconium phosphate particles according to any one of [1] to [5].

[7] A basic gas deodorant for fibers, the deodorant including the zirconium phosphate particles according to any one of [1] to [5].

[8] A basic gas deodorant for fiber kneading, the deodorant including the zirconium phosphate particles according to any one of [1] to [5].

[9] A composition for basic gas deodorizing processing, the composition including the zirconium phosphate particles according to any one of [1] to [5].

[10] A basic gas deodorizing resin composition, the composition including the zirconium phosphate particles according to any one of [1] to [5].

[11] Basic gas deodorizing fibers, including the zirconium phosphate particles according to any one of [1] to [5].

[12] The basic gas deodorizing fibers according to [11], including at least one fiber selected from the group consisting of polyester, polyurethane, nylon, rayon, cotton, acryl, aramid, vinyl on, polyethylene and polypropylene.

[13] A method of producing the zirconium phosphate particles according to any one of [1] to [5], the method including bringing α-zirconium phosphate particles into contact with a basic liquid having a pH of 9 or higher and then further bringing the particles into contact with an acidic liquid having a pH of 6 or lower.

[14] The method of producing zirconium phosphate particles according to [13], in which the basic liquid includes at least one of an alkali metal or an alkaline earth metal.

[15] A method of producing a basic gas deodorizing resin composition, the method including mixing the zirconium phosphate particles obtained by the production method according to [13] or [14] and a resin.

[16] A method of producing a basic gas deodorizing resin composition, the method including:
  bringing zirconium phosphate particles into contact with a basic liquid having a pH of 9 or higher and then further bringing the particles into contact with an acidic liquid having a pH of 6 or lower, to obtain liquid-treated zirconium phosphate particles; and
  mixing the liquid-treated zirconium phosphate particles and a resin.

[17] A method of producing basic gas deodorizing fibers, the method including spinning the basic gas deodorizing resin composition obtained by the production method according to [15] or [16].

[18] A method of producing a basic gas deodorizing resin composition, the method including bringing a resin that includes zirconium phosphate particles into contact with a basic liquid having a pH of 9 or higher and then bringing the resin into contact with an acidic liquid having a pH of 6 or lower.

[19] The method of producing a basic gas deodorizing resin composition according to [18], in which the zirconium phosphate particles are the zirconium phosphate particles according to any one of [1] to [5].

[20] A method of producing basic gas deodorizing fibers, the method including bringing fibers that include zirconium phosphate particles into contact with a basic liquid having a pH of 9 or higher and then bringing the fibers into contact with an acidic liquid having a pH of 6 or lower.

[21] The method of producing basic gas deodorizing fibers according to [20], in which the zirconium phosphate particles are the zirconium phosphate particles according to any one of [1] to [5].

Advantageous Effects of Invention

According to one embodiment of the present invention, zirconium phosphate particles that have high deodorizing performance with respect to a basic gas such as ammonia and trimethylamine and are particularly excellent in deodorizing rate with respect to ammonia, as well as a deodorant, a composition for deodorizing processing, a deodorizing resin composition and deodorizing fibers, each using the particles, and a production method thereof are provided.

DESCRIPTION OF EMBODIMENTS

The present disclosure will be described in detail below.

In the present specification, "%" means "% by weight", "parts" means "parts by weight", and "ppm" means "volume ppm", unless otherwise specified.

Further, in the present specification, the description "X (lower limit) to Y (upper limit)" representing a numerical range means "X or more and Y or less", and the description "Y (upper limit) to X (lower limit)" means "Y or less and X or more". Accordingly, they each represent a numerical range that include the upper limit and the lower limit.

Further, in the present specification, "normal temperature" means 25±5° C.

Further, in the present disclosure, a combination of two or more of the preferred embodiments described below is also a preferred embodiment.

The zirconium phosphate particles in the present disclosure are particles including zirconium phosphate as a main component, and may contain impurities, moisture, or the like, incorporated deriving from the raw material, the production process, and the like. The main component means that a zirconium phosphate component included in the particles is in an amount of 50% by weight or more, preferably 80% by weight or more, more preferably 90% by weight or more, and still more preferably 95% by weight or more.

1. Zirconium Phosphate Particles

The zirconium phosphate particles according to a first aspect of the present disclosure are zirconium phosphate particles, obtained by bringing α-zirconium phosphate particles into contact with a basic liquid having a pH of 9 or higher (hereinafter, also simply referred to as "basic liquid") and then further bringing the particles into contact with an acidic liquid having a pH of 6 or lower (hereinafter, also simply referred to as "acidic liquid").

The zirconium phosphate particles according to a second aspect of the present disclosure are zirconium phosphate particles, in which, after leaving for 10 minutes from putting 10 mg of zirconium phosphate particles and 3 L of air that contains 1,000 ppm of an ammonia gas into a test bag at normal temperature and normal pressure, an ammonia gas reduction rate (X; unit %) represented by Formula (1) below within the test bag that contains the zirconium phosphate particles is 50% or more:

$$X = \{(A_0 - A_1)/A_0\} \times 100 \qquad \text{Formula (1):}$$

in which, in Formula (1), $A_0$ means an ammonia gas concentration in the test bag that does not contain zirconium phosphate particles, and $A_1$ means an ammonia gas concentration in the test bag that contains the zirconium phosphate particles.

In the present specification, the "zirconium phosphate particles of the present disclosure" encompass the zirconium phosphate particles according to the first aspect and the zirconium phosphate particles according to the second aspect.

1-1. Zirconium Phosphate Particles According to First Aspect

The zirconium phosphate particles according to the first aspect are zirconium phosphate particles obtained by bringing α-zirconium phosphate particles into contact with a basic liquid and then further bringing the particles into contact with an acidic liquid.

Hereinafter, the basic liquid, the acidic liquid, the raw material α-zirconium phosphate particles, and the method of producing zirconium phosphate will be described.

1-1-1. Basic Liquid

The base included in the basic liquid is not particularly limited and, for example, a well-known base including an alkali metal, an alkaline earth metal, ammonia, an amine, an ammonium salt, and the like can be used. Examples of the alkali metal include lithium, sodium and potassium, examples of the alkaline earth metal include magnesium and calcium, examples of the amine include an alkylamine such as methylamine, dimethylamine, and trimethylamine, an arylamine such as aniline and methylamine, and a heterocyclic aromatic amine such as pyridine, and examples of the ammonium salt include tetramethylammonium hydroxide. These may be used singly or in combination of two or more.

Among these, it is preferable to use a base that includes at least one selected from an alkali metal or an alkaline earth metal, from the viewpoints of strong alkalinity, enabling efficient performance of contact treatment with a basic liquid, negligible odor, and a favorable working environment. Examples of the base including an alkali metal include lithium hydroxide, sodium hydroxide, and potassium hydroxide, and examples of the base including an alkaline earth metal include magnesium hydroxide and calcium hydroxide.

The solvent used for the basic liquid having a pH of 9 or higher is not particularly limited, and is preferably water or a lower alcohol such as methanol, and more preferably water. The method of preparing the basic liquid having a pH of 9 or higher is not particularly limited, and a well-known method can be applied. For example, the basic liquid can be prepared by dissolving, in a solvent such as water, a base including at least one of an alkali metal or an alkaline earth metal, specifically, lithium hydroxide, sodium hydroxide, potassium hydroxide, magnesium hydroxide, calcium hydroxide or the like, or tetramethylammonium hydroxide or the like.

The pH of the basic liquid is not particularly limited as long as it satisfies 9 or higher, and is preferably 12 or higher and more preferably 13 or higher from the viewpoints of efficiency of the production process and resource saving.

Further, the total amount of the base such as at least one of an alkali metal or an alkaline earth metal when bringing α-zirconium phosphate particles into contact with the basic liquid is preferably 1/20 molar ratio or more, more preferably 1/10 molar ratio or more, and still more preferably 1/5 molar ratio or more, with respect to hydroxy groups that are bonded to phosphorus atoms of the α-zirconium phosphate (hereinafter, also referred to as "P—OH groups"). When the ratio is 1/20 molar ratio or more, the effect of imparting high-speed deodorizing property to α-zirconium phosphate can be sufficiently obtained.

1-1-2. Acidic Liquid

The acid used for the acidic liquid is not particularly limited, and examples thereof include a well-known acid such as hydrochloric acid, nitric acid, sulfuric acid and phosphoric acid. An acid that has an acid dissociation index (accordingly, pKa) smaller than that of the phosphoric acid group of the α-zirconium phosphate is preferable.

The solvent used for the acidic liquid is not particularly limited, and is preferably water or a lower alcohol such as methanol, and more preferably water.

The pH of the acidic liquid is not particularly limited as long as it satisfies 6 or lower, and is preferably 2 or lower and more preferably 1 or lower from the viewpoints of efficiency of the production process and resource saving.

Further, the total amount of the acid when bringing the zirconium phosphate particles into contact with the acidic liquid is preferably 100 mol % or greater, more preferably 300 mol % or greater, still more preferably 1,000 mol % or greater, with respect to the amount of P—OH groups of the α-zirconium phosphate before brought into contact with the basic liquid having a pH of 9 or higher. When the amount is 100 mol % or greater, the effect of imparting high-speed deodorizing property to α-zirconium phosphate can be sufficiently obtained.

1-1-3. α-Zirconium Phosphate Particles

Various compounds can be used as the raw material α-zirconium phosphate that is used in the production of the zirconium phosphate according to the first aspect, and a conventionally well-known α-zirconium phosphate can be used.

As the α-zirconium phosphate, various compounds can be used, and a compound represented by Formula (3) below and having a cation exchange capacity per unit weight of 6.7 meq/g is preferable.

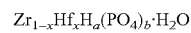   Formula (3):

In Formula (3), a and b are each positive numbers that satisfy 3b−a=4, b is 2.0<b≤2.1, x is a positive number of 0≤x≤0.2, and n is a positive number of 0≤n≤2.0.

In Formula (3) above of the α-zirconium phosphate, hafnium (Hf) is derived from a raw material zirconium compound. In Formula (3), x is a positive number of 0≤x≤0.2. In the present disclosure, x is preferably 0≤x≤0.2, more preferably 0.005≤x≤0.1, and still more preferably 0.005≤x<0.03.

In Formula (3), n is preferably 2.0 or less, and more preferably 1.0 or less. By configuring the value of n to be 2.0 or less, it is possible to prevent attached water or crystallization water from desorbing, which causes foaming or yarn breakage, when melting the resin during spinning.

The method of adjusting the particle size of the zirconium phosphate particles according to the first aspect is not particularly limited. For example, the particle size can be adjusted at any stage before and after brought into contact with the basic liquid having a pH of 9 or higher, and after brought into contact with the acidic liquid having a pH of 6 or lower, and it is preferable to control before brought into contact with the basic liquid having a pH of 9 or higher, accordingly, at the stage of producing the raw material α-zirconium phosphate particles.

The method of adjusting the particle size of the α-zirconium phosphate particles used in the present disclosure is not limited and, in order to obtain the desired particle size distribution, it is preferable to adjust by synthesizing the α-zirconium phosphate particles in an aqueous solution. When synthesized in an aqueous solution, it is easy to make the particle size uniform during the synthesis and easy to obtain a sharp particle size distribution. On the other hand, when the particle size is adjusted by pulverization, fine powder and large particles can also be included, broadening the width of the particle size distribution, which is likely to cause yarn breakage during spinning in the case of kneading into fibers for use as deodorizing fibers.

The α-zirconium phosphate particles used in the present disclosure can be produced by a well-known method. In the method of producing the α-zirconium phosphate, a conventional technique can be applied and there are no restrictions on raw materials, equipment, and the like. For example, examples thereof can include the method described in Japanese Patent Publication No. 5,545,328 and Japanese Patent Publication No. 5,821,258.

The method of producing the α-zirconium phosphate particles is preferably a method of allowing raw material compounds to be reacted with each other in an aqueous solution since particles having a uniform particle size can be easily obtained.

Examples thereof include a method of mixing an aqueous solution of a zirconium compound with an aqueous solution that contains at least one of phosphoric acid or a salt thereof [hereinafter, also referred to as "phosphoric acid (salt)"] to form a precipitate, and aging it to be crystallized.

Examples of the zirconium compound as a production raw material of the α-zirconium phosphate particles include zirconium nitrate, zirconium acetate, zirconium sulfate, zirconium carbonate, basic zirconium sulfate, zirconium oxysulfate, and zirconium oxychloride. Zirconium nitrate, zirconium acetate, zirconium sulfate, zirconium carbonate, basic zirconium sulfate, zirconium oxysulfate and zirconium oxychloride are preferable, and zirconium oxychloride is more preferable in consideration of reactivity, economic efficiency, and the like.

Examples of the phosphoric acid (salt) as the production raw material include phosphoric acid, sodium phosphate, potassium phosphate, and ammonium phosphate, and phosphoric acid is preferable.

The reaction ratio of the phosphoric acid (salt) is, for example, 2 or more, preferably 2.05 or more, and more preferably 2.1 or more in terms of molar ratio charged with respect to the zirconium compound.

The reaction ratio of the phosphoric acid (salt) may be a large excess with respect to the zirconium compound but, considering the conductivity of the supernatant during washing with water after synthesis, the ratio is, for example, 3 or less, preferably 2.9 or less, and more preferably 2.6 or less in terms of the above-described molar ratio, from the viewpoint of improving the efficiency of the washing process with water.

In the production of the α-zirconium phosphate particles, it is preferable to add a dicarboxylic acid (which may be in the form of a hydrate) or a salt thereof in the reaction system, examples of which include oxalic acid, malonic acid, oxalic acid, and a salt thereof. Among them, it is preferable to add oxalic acid or a salt, thereof since the production of the α-zirconium phosphate becomes faster, the waste of raw materials is reduced, and the production can be performed efficiently.

Examples of oxalic acid or a salt thereof in this case include oxalic acid dihydrate, ammonium oxalate, and ammonium hydrogen oxalate, and oxalic acid dihydrate is preferable.

The reaction ratio of oxalic acid or a salt thereof is, for example, from 1.0 to 3.5, more preferably from 1.5 to 3.2, and still more preferably from 2.0 to 3.0, in terms of molar ratio with respect to the zirconium compound. In the present disclosure, a ratio falling within the range described above is preferable since the production of the α-zirconium phosphate becomes easy.

In the production of the α-zirconium phosphate particles, the aqueous solution of a zirconium compound and the aqueous solution that contains phosphoric acid (salt) are mixed, and then aged. The aging may be carried out at room temperature, and is preferably carried out at a wet normal pressure of 90° C. or higher in order to promote the aging. Further, the synthesis may be carried out under a condition of exceeding 100° C. under a pressurized atmosphere higher than normal pressure, accordingly, under a so-called hydrothermal condition. When the α-zirconium phosphate particles are produced under the hydrothermal condition, it is preferable to synthesize them at 130° C. or lower from the viewpoint of production cost.

The production duration of the α-zirconium phosphate particles may be any duration as long as the α-zirconium phosphate particles can be synthesized. For example, the α-zirconium phosphate particles can be obtained by mixing phosphoric acid (salt) and a zirconium compound to cause precipitation and then aging. The aging duration depends on the aging temperature and is appropriately selected.

For example, in the aging at 90° C., the aging duration is preferably 4 hours or longer. Even if aging is performed for 24 hours or longer, the content ratio of the α-zirconium phosphate particles tends to level off.

The α-zirconium phosphate particles after synthesis can be further filtered, washed well with water, and dried to provide α-zirconium phosphate particles.

1-1-4. Method of Producing Zirconium Phosphate Particles

The method of producing zirconium phosphate particles according to the first aspect includes bringing α-zirconium phosphate particles into contact with a basic liquid having a pH of 9 or higher and then further bringing the particles into contact with an acidic liquid having a pH of 6 or lower.

The configurations of the basic liquid, the acidic liquid, and the raw material α-zirconium phosphate particles are as described above, and the preferred ranges are also as described above, respectively.

Each of the temperature when bringing the α-zirconium phosphate particles into contact with the basic liquid and the temperature when further bringing the particles into contact with the acidic liquid is not particularly limited, and is usually carried out in a range of, for example, from 0 to 100° C. Each of the temperatures is preferably in a range of from 10 to 90° C., and more preferably in a range of from 15 to 85° C.

Depending on the purpose, the contact with the basic liquid and the contact with the acidic liquid can be performed at different temperatures from each other.

Each of the method of bringing the α-zirconium phosphate particles into contact with the basic liquid and the method of, after the contact with the basic liquid, further bringing the particles into contact with the acidic liquid is not particularly limited, and a well-known method can be applied to both of them.

Examples thereof include a method of immersing the α-zirconium phosphate particles in each of these liquids, a method of immersing the α-zirconium phosphate particles in each of these liquids and stirring them, and a method of spraying, dropping, or applying each of these liquids to the α-zirconium phosphate particles. These may be carried out singly or in combination, and a method of immersing the particles in each liquid and stirring them is preferable since the contact treatment can be sufficiently performed.

The duration for bringing the α-zirconium phosphate particles into contact with the basic liquid can be appropriately set according to the kind and pH of the basic liquid to be used, the contact temperature, the use of the zirconium phosphate particles to be finally obtained, and the like. The duration for bringing the α-zirconium phosphate particles into contact with the basic liquid is preferably from 3 minutes to 10 hours, more preferably from 15 minutes to 5 hours, and still more preferably from 30 minutes to 3 hours. The contact may be performed for longer than 10 hours according to the kind and pH of the basic liquid to be used, the contact temperature, the use of the zirconium phosphate particles to be finally obtained, and the like, but 10 hours or shorter is economically preferable since the production efficiency is improved. Further, the contact treatment for 3 minutes or longer is preferable since the α-zirconium phosphate particles tend to be uniformly brought into contact with the basic liquid.

The duration for bringing into contact with the acidic liquid after bringing into contact with the basic liquid can be appropriately set according to the kind and pH of the acidic liquid to be used, the contact temperature, the use of the zirconium phosphate particles to be finally obtained, and the like. The duration for bringing into contact with the acidic liquid after bringing into contact with the basic liquid is preferably from 3 minutes to 10 hours, more preferably from 15 minutes to 5 hours, and still more preferably from 30 minutes to 3 hours. The contact may be performed for longer than 10 hours according to the kind and pH of the acidic liquid to be used, the contact temperature, the use of the zirconium phosphate particles to be finally obtained, and the like, but 10 hours or shorter is economically preferable since the production efficiency is improved. Further, the contact treatment for 3 minutes or longer is preferable since the α-zirconium phosphate particles tend to be uniformly brought into contact with the acidic liquid.

1-2. Zirconium Phosphate Particles According to Second Aspect

The zirconium phosphate particles according to the second aspect are zirconium phosphate particles, in which, after leaving for 10 minutes from putting 10 mg of zirconium phosphate particles and 3 L of air that contains 1,000 ppm of an ammonia gas into a test bag at normal temperature and normal pressure, an ammonia gas reduction rate (X; unit %) represented by Formula (1) below within the test bag that contains the zirconium phosphate particles is 50% or more:

$$X=\{(A_0-A_1)/A_0\}\times 100 \quad \text{Formula (1):}$$

in which, in Formula (1), $A_0$ means an ammonia gas concentration in the test bag that does not contain zirconium phosphate particles, and $A_1$ means an ammonia gas concentration in the test bag that contains the zirconium phosphate particles.

The zirconium phosphate particles according to the second aspect preferably have an ammonia gas reduction rate represented by Formula (1) above after leaving for 10 minutes of 55% or more, and more preferably 60% or more.

The zirconium phosphate particles according to the second aspect are preferably zirconium phosphate particles, in which, after leaving for 5 minutes from putting 10 mg of zirconium phosphate particles and 3 L of air that contains 1.000 ppm of an ammonia gas into a test bag at normal temperature and normal pressure, an ammonia gas reduction rate (X; unit %) represented by Formula (1) above is 40% or more, more preferably 50% or more, and still more preferably 55% or more.

The material of the test bag that is used to determine the ammonia gas reduction rate in the present disclosure is not particularly limited, and a well-known material can be used. Examples thereof include polyvinyl alcohol, polyvinylidene fluoride, polyvinyl fluoride, an ethylene tetrafluoride/propylene hexafluoride copolymer, and polyester.

A well-known method can be applied as the method of detecting the concentration of a basic gas such as ammonia in the present disclosure, and there is no particular limitation. For example, the concentration of an ammonia gas can be measured using a gas sampler and a detector tube. Specifically, a detector tube for detecting ammonia gas in which a syringe needle has been installed is attached to a gas sampler and inserted into the test bag, the ammonia gas is sucked by the suction power of the gas sampler and adsorbed to the detector tube, and the concentration value is read from the change in color of the detector tube, whereby the measurement can be performed.

1-2-1. Method of Producing Zirconium Phosphate Particles

The method of producing the zirconium phosphate particles according to the second aspect is not particularly limited. For example, the particles may be produced by the method of producing the zirconium phosphate particles according to the first aspect described above.

1-3. Median Diameter

The median diameter of primary particles of the zirconium phosphate particles of the present disclosure (hereinafter, also simply referred to as "particle size") is preferably from 0.1 to 10.0 μm, more preferably from 0.2 to 3.0 μm, and still more preferably from 0.2 to 1.5 μm. The median diameter of primary particles is preferably from 0.2 to 1.5 μm, since the number of particles is larger when kneaded into fibers and the deodorizing effect is easily obtained. Further, a median diameter of primary particles of 0.1 μm or more is preferable, since the particles are unlikely to aggregate and tend not to cause yarn breakage during spinning.

The particle size in the present disclosure indicates a value obtained by carrying out measurement by means of a laser diffraction particle size distribution meter and analyzing the result in terms of volume basis.

The method of adjusting the particle size of the zirconium phosphate particles of the present disclosure is not particularly limited. For example, the particle size can be adjusted in the method of producing the zirconium phosphate particles described above.

1-4. Dry Reduction Rate

The high-speed deodorizing zirconium phosphate particles of the present disclosure preferably have a dry reduction rate (Y; unit % by weight) represented by Formula (2) below after heating at 150° C. for 2 hours under normal pressure of 5.0% by weight or less, more preferably 3.0% by weight or less, and still more preferably 1.0% by weight or less.

The dry reduction rate of 5.0% by weight or less is preferable, since foaming and hydrolysis of a resin can be reduced during the production of a masterbatch of the deodorizing resin composition or the deodorizing fibers including the high-speed deodorizing zirconium phosphate particles.

$$Y=\{(B_0-B_1)/B_0\}100 \quad \text{Formula (2):}$$

In Formula (2), $B_0$ means a weight of the zirconium phosphate particles before heating, and $B_1$ means a weight of the zirconium phosphate particles after heating.

2. Applications

The zirconium phosphate particles of the present disclosure can be used for various applications.

In particular, the zirconium phosphate particles of the present disclosure can be preferably used as a basic gas adsorbent since the adsorption rate with respect to a basic gas is high.

Further, the zirconium phosphate particles of the present disclosure can be preferably used as a deodorant, and more preferably used as a basic gas deodorant.

Examples of the basic gas include ammonia, an alkylamine such as trimethylamine, and dimethylamine, a nitrogen-containing heteroaromatic compound such as pyridine, a heterocyclic amine such as piperidine, an aromatic amine such as aniline, and a hydrazine, each of which causes odors.

Further, the basic gas deodorant can be preferably used as a basic gas deodorant for fibers and a basic gas deodorant for fiber kneading.

The specific usage thereof will be described in detail below.

3. Composition for Basic Gas Deodorizing Processing

The high-speed deodorizing zirconium phosphate particles of the present disclosure can be appropriately mixed with a well-known binder, dispersant, oil agent, solvent and the like to configure a composition for basic gas deodorizing processing. By using these, the basic gas deodorant can be spread on fibers, filters, fabrics, sheets and the like, to impart deodorizing property.

The binder is not particularly limited, and a well-known binder can be used. For example, the binder is a component that adheres the deodorant including the zirconium phosphate particles of the present disclosure to a substrate such as fibers in the production of the deodorizing product. The binder is preferably a polymer compound, and may be any of a synthetic polymer compound, a semi-synthetic polymer compound, and a natural polymer compound.

Examples of the polymer compound include a resin and a polysaccharide, and a resin is preferable. The binder that may be included in the composition for basic gas deodorizing processing of the present disclosure may be one kind or two or more kinds. The resin may be either a water-soluble resin or a water-insoluble resin, and examples thereof include an ethylene/vinyl acetate copolymer or a modified product thereof (for example, an acid modified product), an ethylene/vinyl chloride copolymer, a vinyl chloride/vinyl acetate copolymer, polyvinyl acetate, polyvinyl chloride, a modified olefin resin (for example, a chlorinated polyolefin), polyvinyl alcohol, an alkyl cellulose, a carboxyalkyl cellulose, a carboxyalkyl hydroxyalkyl cellulose, polyacrylic acid, a polyacrylic acid salt, an acrylic resin, a polyester resin, an urethane resin, a styrene/butadiene copolymer, a styrene/isoprene copolymer, a styrene/butadiene/styrene block copolymer, a styrene/ethylene/butylene/styrene block copolymer, a styrene/ethylene/propylene/styrene block copolymer, a hydrogenated styrene/butadiene/styrene block copolymer, a hydrogenated styrene/ethylene/butylene/styrene block copolymer, a hydrogenated styrene/ethylene/propylene/styrene block copolymer, and a styrene/anhydrous maleic acid copolymer.

The dispersant is not particularly limited and a well-known dispersant can be used. For example, any one of an anionic surfactant, a cationic surfactant, a zwitterionic surfactant and a nonionic surfactant may be used, or two or more kinds thereof may be used in combination. Of these, an anionic surfactant and a nonionic surfactant are particularly preferable from the viewpoint of dispersibility of the zirconium phosphate particles. The preferred surfactant that may be contained in the composition for basic gas deodorizing processing of the present disclosure may be either an anionic surfactant or a nonionic surfactant, or may be both of them.

The composition for bask gas deodorizing processing of the present disclosure may contain a medium. The medium is not particularly limited, and examples thereof include water alone or a mixed solution of water and a water-soluble organic solvent, and water is preferable.

Examples of the water-soluble organic solvent include a lower alcohol such as methanol, ethanol and 2-propanol.

4. Basic Gas Deodorizing Resin Composition

The high-speed deodorizing zirconium phosphate particles of the present disclosure can be mixed with a resin to configure a basic gas deodorizing resin composition. Examples of the resin include, but are not limited to, polypropylene, polyethylene, acrylonitrile/butadiene/styrene (ABS), polyester, polyurethane, nylon, polystyrene, polycarbonate, an acrylic resin, and a vinyl chloride resin.

The method of producing the basic gas deodorizing resin composition is not particularly limited.

For example, the composition may be produced by a method including mixing a resin, and the zirconium phosphate particles obtained by the method of producing the zirconium phosphate particles described above.

Further, the composition may be produced by a method including: bringing zirconium phosphate particles into contact with a basic liquid having a pH of 9 or higher and then further bringing the particles into contact with an acidic liquid having a pH of 6 or lower, to obtain liquid-treated zirconium phosphate particles; and mixing the liquid-treated zirconium phosphate particles and a resin.

The method of mixing the zirconium phosphate particles and the resin is not particularly limited, and kneading the zirconium phosphate particles into the resin is preferable from the viewpoint of imparting durability or abrasion resistance so that the zirconium phosphate does not fall off from the resin, to maintain deodorizing performance.

5. Basic Gas Deodorizing Fibers

The basic gas deodorizing fibers of the present disclosure are not particularly limited as long as they include the zirconium phosphate particles of the present disclosure or include the basic gas deodorant that includes the particles.

The method of producing the basic gas deodorizing fibers of the present disclosure may be in accordance with a conventional method.

Examples thereof include a method of kneading the basic gas deodorant of the present disclosure into fibers and spinning them, and a method of applying the composition for basic gas deodorizing processing that includes the basic gas deodorant of the present disclosure to spun fibers.

The resin for fibers that can be used for processing the basic gas deodorant of the present disclosure is not particularly limited, and any known chemical fibers can be used. Examples thereof include polyester, polyurethane, nylon, rayon, an acrylic resin, aramid, vinylon, polyethylene, and polypropylene. Of these, polyurethane, polyester, nylon, an acrylic resin and polyethylene are preferable. Each of these resins may be a homopolymer or may be a copolymer. In the case of a copolymer, the polymerization ratio of each copolymerization component is not particularly limited.

The polyurethane may be any material as long as a polymer diol and a diisocyanate are used as starting materials, and is not particularly limited. Further, the synthesis method thereof is not particularly limited.

The polyester is also not particularly limited and, for example, polyethylene terephthalate, polyethylene naphthalate, polytrimethylene terephthalate and polybutylene terephthalate are preferable.

The basic gas deodorant of the present disclosure can be preferably used as a deodorant for fiber kneading.

Specific examples of the method of producing the basic gas deodorizing fibers in this case include: a method of kneading the deodorant of the present disclosure into a molten liquid resin for fibers or a resin solution for fibers with a resin dissolved in a solvent, and spinning; and a method of processing into a master batch resin that contains the basic gas deodorant at a high concentration, followed by mixing and melting with a resin for fibers, and spinning.

The proportion of the basic gas deodorant of the present disclosure that is contained in the resin for fibers is not particularly limited. Generally, if the content is increased, the deodorizing property can be strongly exerted and maintained for a long period of duration. However, from the viewpoint of economic efficiency and the viewpoint that even if the content is increased to a certain extent or more, the deodorizing effect does not differ significantly, and/or the strength of the resin will decrease, the content is preferably from 0.1 to 5.0 parts by weight and more preferably from 0.5 to 2.0 parts by weight per 100 parts by weight of the resin.

The method of producing the basic gas deodorizing resin composition that includes the zirconium phosphate particles of the present disclosure is a method including bringing a resin that includes the zirconium phosphate particles into contact with a basic liquid having a pH of 9 or higher and then bringing the resin into contact with an acidic liquid having a pH of 6 or lower.

The method of producing the basic gas deodorizing fibers that include the zirconium phosphate particles of the present disclosure is a method including bringing fibers that include the zirconium phosphate particles into contact with a basic liquid having a pH of 9 or higher and then bringing the fibers into contact with an acidic liquid having a pH of 6 or lower.

In the present invention, bringing the zirconium phosphate into contact with a basic liquid having a pH of 9 or higher and then further bringing the zirconium phosphate into contact with an acidic liquid having a pH of 6 or lower may take the form of direct contact with the zirconium phosphate, or may be contact with particles kneaded into a resin, fibers, or the like, by which the liquid permeates the resin or the fibers such that the basic liquid and the acidic liquid are brought into contact with the zirconium phosphate in the resin, the fibers, or the like, which fails within the same concept and exerts the same effect.

Examples of the zirconium phosphate particles include a zirconium phosphate having a basic gas adsorbing ability such as α-zirconium phosphate particles, zirconium phosphate particles that are obtained by bringing α-zirconium phosphate particles into contact with a basic liquid having a pH of 9 or higher and then further bringing the particles into contact with an acidic liquid having a pH of 6 or lower, β-zirconium phosphate particles, γ-zirconium phosphate particles, and amorphous zirconium phosphate particles. Preferred examples thereof include α-zirconium phosphate particles, and zirconium phosphate particles that are obtained by bringing α-zirconium phosphate particles into contact with a basic liquid having a pH of 9 or higher and then further bringing the particles into contact with an acidic liquid having a pH of 6 or lower. More preferred examples thereof include zirconium phosphate particles that are obtained by bringing α-zirconium phosphate particles into contact with a basic liquid having a pH of 9 or higher and then further bringing the particles into contact with an acidic liquid having a pH of 6 or lower. That is, in the case of using the zirconium phosphate particles that are liquid-treated products of the α-zirconium phosphate particles, the resin or fibers including the particles are subjected to a second liquid treatment. The second liquid treatment may be substantially a treatment including a dyeing treatment or the like.

A basic gas deodorizing resin composition and basic gas deodorizing fibers including zirconium phosphate particles may deteriorate in the adsorption performance with respect to a basic gas, may be decreased in the deodorizing property, or may not exhibit the deodorizing property, after the contact treatment with a basic liquid in the fiber production process such as dyeing treatment. On the other hand, as described in the present disclosure, by further performing the contact treatment with an acidic liquid after the contact treatment with a basic liquid described above, not only the deodorizing property is exhibited, but also a basic gas deodorizing resin composition and basic gas deodorizing fibers are provided which have improved deodorizing rate with respect to a basic gas compared to a basic gas deodorizing resin composition and basic gas deodorizing fibers after the contact treatment with a basic liquid and before the contact treatment with an acidic liquid of the present disclosure.

6. Additives

The basic gas deodorant, the basic gas deodorant for fibers, the composition for basic gas deodorizing processing, the basic gas deodorizing resin composition, and the basic gas deodorizing fibers, each including the high-speed deodorizing zirconium phosphate particles of the present disclosure, may include an additive as appropriate.

The additive is not particularly limited, and examples thereof include a thickener, other well-known deodorants such as an acidic gas deodorant, a basic gas deodorant, a sulfur gas deodorant, an aldehyde gas deodorant, and a ketone gas deodorant, an antibacterial agent, an antifungal agent, an antiviral processing agent, an antiallergen agent, a defoamer, a colorant, a preservative, a viscosity modifier, and a fragrance agent.

The other well-known deodorants do not encompass the basic gas deodorant of the present disclosure.

The thickener is not particularly limited, and a known thickener can be used. Examples thereof include a polysaccharide, specific examples of which include xanthan gum, alginate, gum arabic, starch, tamarind seed gum, guar gum, and carboxy methyl cellulose.

The other deodorants can be blended of a kind and at a proportion that do not deteriorate the deodorizing performance of the obtained deodorizing product with respect to a basic gas.

Examples of compounds that cause odor include: a basic gas such as an ammonia gas and trimethylamine; an acidic gas such as acetic acid and isovaleric acid; an aldehyde gas such as formaldehyde, acetaldehyde and nonenal; and a sulfur gas such as hydrogen sulfide and methyl mercaptan, and other deodorants having deodorizing performance with respect to these can be contained.

Examples of the deodorant for basic gas include an amorphous composite oxide such as zeolite, $Al_2O_3$, $SiO_2$, MgO, CaO, SrO, BaO, $ZrO_2$, $TiO_2$, $WO_2$, $CeO_2$, $Li_2O$, $Na_2O$, and $K_2O$.

Examples of the deodorant for acidic gas include zirconium hydroxide, zirconium oxide, and a hydrotalcite compound such as magnesium-aluminum hydrotalcite.

Examples of the deodorant for aldehyde gas include a hydrazine compound such as adipic acid dihydrazide, carbohydrazide, succinic dihydrazide and oxalyl dihydrazide, and an aminoguanidine salt such as aminoguanidine hydrochloride, aminoguanidine sulfate and aminoguanidine bicarbonate.

Examples of the deodorant for sulfur gas include copper silicate, zirconium copper phosphate hydrate, zinc oxide, zinc aluminum oxide, zinc silicate, zinc aluminum silicate, and a layered zinc aluminosilicate.

The deodorizing resin composition using the deodorant of the present disclosure can be used in various fields requiring deodorizing property and can be used for many resin products, for example, daily necessities such as trash cans, triangular corners, wraps, and sponges, electric products such as refrigerators, air purifier filters, and air conditioner filters, household building materials such as wallpaper, toilet bowls, toilet seats, kitchen counters, ventilation fan filters, and paints, fiber products such as clothing, bedding, curtains, mats, shoes, stockings, and socks, pet products, and nursing care products.

The deodorizing fiber using the deodorant of the present disclosure can be used in various fields requiring deodorizing property and can be used for many fiber products, for example, underwear, stockings, socks, beddings, bedding covers, cushions, blankets, carpets, curtains, sofas, car seats, air filters and nursing clothing.

EXAMPLES

Hereinafter, the present disclosure will be specifically described based on Examples and Comparative Examples, but the present disclosure is not limited to the following Examples.

Production Example 1 (Production of α-zirconium Phosphate)

To a 2 L round bottom flask, 1,345 mL of deionized water and 135 g of 35% hydrochloric acid were added, 225 g of a 20% aqueous solution of zirconium oxychloride octahydrate containing 0.18% by weight of hafnium was added, and 93 g of oxalic acid dihydrate was then added and dissolved. While stirring the solution well, 101 g of 75% phosphoric acid was added. This was heated to 98° C. over 2 hours and then refluxed with stirring for 12 hours. After cooling the reaction system, the obtained precipitate was collected by filtration, washed well with water, and dried under normal pressure at 105° C. to obtain zirconium phosphate. This was crushed by means of a rotor speed mill (16,000 rpm, sieve mesh 80 μm. As a result of measuring powder X-ray diffraction and fluorescent X-ray analysis of the obtained zirconium phosphate, it was confirmed that the zirconium phosphate was α-zirconium phosphate.

When this α-zirconium phosphate was subjected to fluorescent X-ray analysis and simultaneous measurement of thermogravimetry/differential thermal analysis (TG-DTA), the composition formula was $Zr_{0.99}Hf_{0.01}H_{2.03}(PO_4)_{2.01} \cdot 0.05H_2O$ and the median diameter was 0.89 μm.

The measurement conditions and measurement methods of powder X-ray diffraction, fluorescent X-ray analysis, TG-DTA, and particle size (median diameter) are described below.

<Powder X-ray Diffraction>

D8 ADVANCE, manufactured by BRUKER Co., Ltd., was used as the X-ray diffractometer. The X-ray diffraction diagram was obtained using a Cu-sealed X-ray source and CuKα that is generated at an applied voltage of 40 kV and a current value of 40 mA. The detailed measurement conditions are as follows.

X-ray source: Sealed X-ray source (Cu source), 0.4×12 mm², Long Fine Focus
Rating: 2.2 kW
Output used: 40 kV-40 mA (1.6 kW)
Goniometer radius: 280 mm
Sample stage: FlipStick_Twin_Twin-XE
Measurement range 2θ: 5° to 55°
Step width: 0.02°
Step duration: 0.05 seconds/step
Incident side solar slit: 2.5°
Anti-scattering slit: 10.5 mm
Curvature: 1.00
Detector: LYNXEYE XE
Detector slit width: 5.758 mm
Detector window width: 2.9°

<Fluorescent X-ray Analysis>

The fluorescent X-ray analysis was measured under the following conditions.
Measuring equipment: ZSX Primus II, manufactured by Rigaku
Measurement conditions
Measuring elements: C to U (constant angle measurement for F, Cl, Br, I, BG 4 sec, peak 8 sec)
Analytical diameter: 20 mm
Measurement number: measured at n2
Sample processing: A tablet molding machine was used to pressure-mold the sample into pellets, which were subjected to the measurement.
Analysis
Software: ZSX version 7.49
Model Bulk

<TG-DTA>

The TG-DTA measurement was performed under the following conditions.
Measuring equipment: TG/DTA 6300, manufactured by Hitachi High-Tech Science Measurement method: 7 to 8 mg of the sample was put and set in an Al pan, the temperature was raised to 600° C. at 20° C./min, and the decrease in weight from room temperature to 100° C. was determined as a water content (attached water), and the decrease in weight from 100° C. to 250° C. was estimated as crystallization water.

<Measurement of Particle Size (Median Diameter)>

The particle size of the deodorant was measured by means of a laser diffraction type particle size distribution measuring device "Mastersizer 2000", manufactured by Malvern, and the results were analyzed in terms of volume basis. The deodorant dispersion liquid in which the deodorant was added was dispersed by ultrasonic waves and measured at a refractive index of 2.4.

Example 1

[Usage amount of sodium hydroxide: 1/4 molar ratio with respect to P—OH groups of α-zirconium phosphate, bath ratio: α-zirconium phosphate/NaOH aqueous solution=1/20 weight ratio]

To a 100 mL beaker, 3 g of the α-zirconium phosphate obtained in Production Example 1 and 3 g of pure water were added and stirred with a stirrer, then, 57 g of an aqueous sodium hydroxide solution (1/4 molar ratio with respect to P—OH groups of the α-zirconium phosphate) of which pH was adjusted to 12.9 was added, stirred at 80° C. for 1 hour, and then collected by filtration. Then, after filtering and washing until the electric conductivity of the filtrate becomes 100 μS/cm or less, the obtained zirconium phosphate was dried at 120° C. for 2 hours under normal pressure and pulverized in a Menou dairy pot, to obtain basic liquid-treated zirconium phosphate particles (A-1). Next, to a 200 mL beaker, 200 g of a 1N aqueous nitric acid solution (pH 1) was added, 1.8 g of the basic liquid-treated zirconium phosphate was added thereto, stirred at 80° C. for 2 hours. Then, after filtering and washing until the electric conductivity of the filtrate becomes 100 μS/cm or less as in the same manner as described above, the obtained zirconium phosphate was dried at 120° C. for 2 hours under normal pressure and pulverized in a Menou dairy pot, to obtain acidic liquid-treated zirconium phosphate particles (A-2). When adjusting the pH, SD-51 pH meter, manufactured by HORIBA, was used.

The median diameter of A-2 was measured according to the method described above, and the dry reduction rate was measured according to the method indicated in (1) below. The results are shown in Table 1.

Further, the performance of A-2 as a deodorant was measured according to the method indicated in (2) below. The results are shown in Table 1.

(1) Measurement of Dry Reduction Rate (%)

The dry reduction rate of the deodorant particles was measured by the first method of 4.1.1 (1) of ifs K 0067:1992 (test method of weight reduction and residue of chemical product). The deodorant particles were allowed to stand in a room at a temperature of 25° C. and a humidity of 50% for 24 hours, then heated at 150° C. for 2 hours under normal pressure, the weight before and after heating was measured, and the dry reduction rate (Y; unit % by weight) of the deodorant was calculated from Formula (2) below:

$$Y=\{(B_0-B_1)/B_0\}\times 100 \quad \text{Formula (2):}$$

in which, in Formula (2), $B_0$ means a weight of the zirconium phosphate particles (deodorant) before heating, and $B_1$ means a weight of the zirconium phosphate particles (deodorant) after heating (2) Deodorizing Property Test As a deodorizing test, the deodorizing property with respect to odor components was evaluated by the equipment test as follows.

First, after leaving for 10 minutes at normal temperature and normal pressure from putting 10 mg of the zirconium phosphate particles into a test bag (teller bag) and injecting an ammonia gas and dry air thereto, to set the ammonia gas concentration and the gas volume within the test bag to 1,000 ppm and 3 L, respectively, an ammonia gas reduction rate (X; unit %) within the test bag was calculated by Formula (1) below. In order to calculate the ammonia gas reduction rate, a test bag that does not contain zirconium phosphate particles was also prepared and the ammonia gas concentration after 10 minutes was measured.

$$X=\{(A_0-A_1)/A_0)\}\times 100 \quad \text{Formula (1):}$$

In Formula (1), $A_0$ means an ammonia gas concentration in the test bag that does not contain zirconium phosphate particles, and $A_1$ means an ammonia gas concentration in the test bag that contains the zirconium phosphate particles.

Example 2

[Usage amount of sodium hydroxide: 1/3 molar ratio with respect to P—OH groups of α-zirconium phosphate, bath ratio: α-zirconium phosphate/NaOH aqueous solution=1/20 weight ratio]

Basic liquid-treated zirconium phosphate particles (B-1) and acidic liquid-treated zirconium phosphate particles (B-2) were obtained in the same manner as in Example 1, except that 57 g of an aqueous sodium hydroxide solution (1/3 molar ratio with respect to P—OH groups of the α-zirconium phosphate) of which pH was adjusted to 13.1 was used.

The median diameter, the dry reduction rate, and the deodorizing performance of B-2 were measured and evaluated in the same manner as in Example 1. The results are shown in Table 1.

Example 3

[Usage amount of sodium hydroxide: 1/2 molar ratio with respect to P—OH groups of α-zirconium phosphate, bath ratio: α-zirconium phosphate/NaOH aqueous solution=1/20 weight ratio]

Basic liquid-treated zirconium phosphate particles (C-1) and acidic liquid-treated zirconium phosphate particles (C-2) were obtained in the same manner as in Example 1, except that 57 g of an aqueous sodium hydroxide solution (1/2 molar ratio with respect to P—OH groups of the α-zirconium phosphate) of which pH was adjusted to 13.3 was used.

The median diameter, the dry reduction rate, and the deodorizing performance of C-2 were measured and evaluated in the same manner as in Example 1. The results are shown in Table 1.

Example 4

[Usage amount of sodium hydroxide: 1/1.5 molar ratio with respect to P—OH groups of α-zirconium phosphate, bath ratio: α-zirconium phosphate/NaOH aqueous solution=1/20 weight ratio]

Basic liquid-treated zirconium phosphate particles (D-1) and acidic liquid-treated zirconium phosphate particles (D-2) were obtained in the same manner as in Example 1, except that 57 g of an aqueous sodium hydroxide solution (1/1.5 molar ratio with respect to P—OH groups of the α-zirconium phosphate) of which pH was adjusted to 13.4 was used.

The median diameter, the dry reduction rate, and the deodorizing performance of D-2 were measured and evaluated in the same manner as in Example 1. The results are shown in Table 1.

Example 5

[Usage amount of sodium hydroxide: 1/1 molar ratio with respect to P—OH groups of α-zirconium phosphate, bath ratio: α-zirconium phosphate/NaOH aqueous solution=1/20 weight ratio]

Basic liquid-treated zirconium phosphate particles (E-1) and acidic liquid-treated zirconium phosphate particles (E-2) were obtained in the same manner as in Example 1, except that 57 g of an aqueous sodium hydroxide solution (1/1 molar ratio with respect to P—OH groups of the α-zirconium phosphate) of which pH was adjusted to 13.6 was used.

The median diameter, the dry reduction rate, and the deodorizing performance of E-2 were measured and evaluated in the same manner as in Example 1. The results are shown in Table 1.

Example 6

[Usage amount of sodium hydroxide: 1/3 molar ratio with respect to P—OH groups of α-zirconium phosphate, bath ratio: α-zirconium phosphate/NaOH aqueous solution=1/5 weight ratio]

Basic liquid-treated zirconium phosphate particles (F-1) and acidic liquid-treated zirconium phosphate particles (F-2) were obtained in the same manner as in Example 1, except that 9 g of the α-zirconium phosphate obtained in Production Example 1, 9 g of pure water, and 36 g of an aqueous sodium hydroxide solution (1/3 molar ratio with respect to P—OH groups of the α-zirconium phosphate) of which pH was adjusted to 13.8 were used.

The median diameter, the dry reduction rate, and the deodorizing performance of F-2 were measured and evaluated in the same manner as in Example 1. The results are shown in Table 1.

Example 7

[Usage amount of sodium hydroxide: 1/2 molar ratio with respect to P—OH groups of α-zirconium phosphate, bath ratio: α-zirconium phosphate/NaOH aqueous solution 1/5 weight ratio]

Basic liquid-treated zirconium phosphate particles (G-1) and acidic liquid-treated zirconium phosphate particles (G-2) were obtained in the same manner as in Example 6, except that 36 g of an aqueous sodium hydroxide solution (1/2 molar ratio with respect to P—OH groups of the α-zirconium phosphate) of which pH was adjusted to 13.9 was used.

The median diameter, the dry reduction rate, and the deodorizing performance of G-2 were measured and evaluated in the same manner as in Example 1. The results are shown in Table 1.

Example 8

[Usage amount of sodium hydroxide: 1/1.5 molar ratio with respect to P—OH groups of α-zirconium phosphate, bath ratio: α-zirconium phosphate/NaOH aqueous solution=1/5 weight ratio]

Basic liquid-treated zirconium phosphate particles (H-1) and acidic liquid-treated zirconium phosphate particles (H-2) were obtained in the same manner as in Example 6, except that 36 g of an aqueous sodium hydroxide solution (1/1.5 molar ratio with respect to P—OH groups of the α-zirconium phosphate) of which pH was adjusted to 14.0 was used.

The median diameter, the dry reduction rate, and the deodorizing performance of H-2 were measured and evaluated in the same manner as in Example 1. The results are shown in Table 1.

Comparative Example 1

[α-Zirconium Phosphate]

The median diameter, the dry reduction rate, and the deodorizing performance of the α-zirconium phosphate particles obtained in Production Example 1 were measured and evaluated in the same manner as in Example 1. The results are shown in Table 1.

charged into a fully automatic injection molding machine (model: M-50A II-DM, manufactured by Meiki Seisakusho) that was set at 270° C., to prepare an injection molded plate with 11 cm×11 cm×1 mm. Then, this plate was pulverized by means of a wonder blender (model: WB-1, manufactured by Osaka Chemical Co., Ltd.) so that the median diameter was 200 μm±100 μm, to obtain a zirconium phosphate-kneaded resin composition A. The deodorizing performance thereof was evaluated according to the method indicated in "(3) Deodorizing property test-2" described below. The results are shown in Table 2.

Comparative Example 2

A zirconium phosphate-kneaded resin composition B was obtained in the same manner as in Example 9, except that 3% by weight of the α-zirconium phosphate used in Comparative Example 1 and 97% by weight of a polyester resin (MA-2101M, manufactured by Unitica. Co., Ltd.) that was dried at 150° C. for 12 hours were mixed. The deodorizing performance thereof was evaluated according to the method indicated in "(3) Deodorizing property test-2" described below. The results are shown in Table 2.

(3) Deodorizing Property Test-2

After leaving for 1 hour at normal temperature and normal pressure from putting 2.4 g of the zirconium phosphate-kneaded resin composition into a test bag (tedler bag) and injecting dry air and an ammonia gas thereto, to set the ammonia gas concentration and the gas volume within the test bag to 100 ppm and 3 L, respectively, an ammonia gas reduction rate within the test bag after leaving was calcu-

TABLE 1

| | Zirconium phosphate particles and production method | | | | | | | Deodorizing performance test | |
|---|---|---|---|---|---|---|---|---|---|
| | Zirconium phosphate particles | NaOH/ P—OH group molar ratio | Zirconium phosphate/NaOH aqueous solution bath ratio (weight ratio) | pH of NaOH aqueous solution used for basic liquid treatment | pH of nitric acid aqueous solution used for acidic liquid treatment | Particle properties | | Ammonia gas reduction rate after 5 minutes (%) | Ammonia gas reduction rate after 10 minutes (%) |
| | | | | | | Median diameter (μm) | Dry reduction rate (%) | | |
| Example 1 | A-2 | 1/4 | 1/20 | 12.9 | 1 | 0.9 | 2.6 | 53 | 59 |
| Example 2 | B-2 | 1/3 | | 13.1 | 1 | 1 | 2.3 | 56 | 60 |
| Example 3 | C-2 | 1/2 | | 13.3 | 1 | 0.9 | 2.3 | 47 | 55 |
| Example 4 | D-2 | 1/1.5 | | 13.4 | 1 | 1.1 | 2.4 | 54 | 59 |
| Example 5 | E-2 | 1/1 | | 13.6 | 1 | 2.7 | 2.9 | 41 | 50 |
| Example 6 | F-2 | 1/3 | 1/5 | 13.8 | 1 | 0.9 | 2.8 | 55 | 59 |
| Example 7 | G-2 | 1/2 | | 13.9 | 1 | 1.1 | 2.1 | 42 | 55 |
| Example 8 | H-2 | 1/1.5 | | 14.0 | 1 | 0.9 | 2.3 | 56 | 60 |
| Comparative Example 1 | α-Zirconium phosphate particles | | | Untreated | Untreated | 0.9 | 2.8 | 31 | 40 |

Example 9

3% by weight of the acid-treated zirconium phosphate (G-2) obtained in Example 7 and 97% by weight of a polyester resin (MA-2101M, manufactured by Unitica Co., Ltd.) that was dried at 150° C. for 12 hours were mixed, and lated by Formula (1) above. Here, $A_0$ in Formula. (1) means an ammonia gas concentration in the test bag that does not contain zirconium phosphate-kneaded resin composition, and $A_1$ means an ammonia gas concentration in the test bag that contains the zirconium phosphate-kneaded resin composition.

TABLE 2

| Test sample<br>Zirconium phosphate-<br>kneaded resin composition | Deodorizing performance<br>test result<br>Ammonia gas reduction<br>rate after 1 hours (%) |
|---|---|
| Example 9 | A | 80 |
| Comparative<br>Example 2 | B | 58 |

The disclosure of Japanese Patent Application No. 2020-044208, filed. Mar. 13, 2020, is incorporated herein by reference in its entirety.

All publications, patent applications, and technical standards described in the present specification are herein incorporated by reference to the same extent as if each individual publication, patent application, or technical standard was specifically and individually indicated to be incorporated by reference.

Industrial Applicability

The zirconium phosphate particles of the present disclosure can be preferably used for a deodorant, and the deodorant has a high adsorption rate with respect to a basic gas such as ammonia and is particularly excellent in deodorizing performance with respect to ammonia. Therefore, the deodorant can be further used for a composition for deodorizing processing, a deodorizing resin composition, and deodorizing fibers.

Further, the method of producing zirconium phosphate particles of the present disclosure can provide a production method that is capable of improving the deodorizing performance.

What is claimed is:

1. Zirconium phosphate particles, obtained by bringing α-zirconium phosphate particles into contact with a basic liquid having a pH of 9 or higher and then further bringing the particles into contact with an acidic liquid having a pH of 6 or lower.

2. The zirconium phosphate particles according to claim 1, wherein the basic liquid comprises at least one of an alkali metal or an alkaline earth metal.

3. Zirconium phosphate particles, wherein, after leaving for 10 minutes from putting 10 mg of zirconium phosphate particles and 3 L of air that contains 1,000 ppm of an ammonia gas into a test bag at normal temperature and normal pressure, an ammonia gas reduction rate (X; unit %) represented by Formula (1) below within the test bag that contains the zirconium phosphate particles is 50% or more:

$$X=\{(A_0-A_1)/A_0\}\times 100 \quad \text{Formula (1)}:$$

wherein, in Formula (1), $A_0$ means an ammonia gas concentration in the test bag that does not contain zirconium phosphate particles, and $A_1$ means an ammonia gas concentration in the test bag that contains the zirconium phosphate particles.

4. The zirconium phosphate particles according to claim 1, wherein a median diameter of primary particles is from 0.1 to 10 μm.

5. The zirconium phosphate particles according to claim 1, wherein a dry reduction rate (Y; unit % by weight) represented by Formula (2) below after heating at 150° C. for 2 hours is 5.0% by weight or less:

$$Y=\{(B_0-B_1)/B_0\}\times 100 \quad \text{Formula (2)}:$$

wherein, in Formula (2), $B_0$ means a weight of the zirconium phosphate particles before heating, and $B_1$ means a weight of the zirconium phosphate particles after heating.

6. A basic gas deodorant, comprising the zirconium phosphate particles according to claim 1.

7. A basic gas deodorant for fibers, the deodorant comprising the zirconium phosphate particles according to claim 1.

8. A basic gas deodorant for fiber kneading, the deodorant comprising the zirconium phosphate particles according to claim 1.

9. A composition for basic gas deodorizing processing, the composition comprising the zirconium phosphate particles according to claim 1.

10. A basic gas deodorizing resin composition, the composition comprising the zirconium phosphate particles according to claim 1.

11. Basic gas deodorizing fibers, comprising the zirconium phosphate particles according to claim 1.

12. The basic gas deodorizing fibers according to claim 11, comprising at least one fiber selected from the group consisting of polyester, polyurethane, nylon, rayon, cotton, acryl, aramid, vinylon, polyethylene and polypropylene.

13. A method of producing the zirconium phosphate particles according to claim 1, the method comprising bringing α-zirconium phosphate particles into contact with a basic liquid having a pH of 9 or higher and then further bringing the particles into contact with an acidic liquid having a pH of 6 or lower.

14. The method of producing zirconium phosphate particles according to claim 13, wherein the basic liquid comprises at least one of an alkali metal or an alkaline earth metal.

15. A method of producing a basic gas deodorizing resin composition, the method comprising mixing the zirconium phosphate particles obtained by the production method according to claim 13 and a resin.

16. A method of producing basic gas deodorizing fibers, the method comprising spinning the basic gas deodorizing resin composition obtained by the production method according to claim 15.

17. A method of producing a basic gas deodorizing resin composition, the method comprising bringing a resin that comprises zirconium phosphate particles into contact with a basic liquid having a pH of 9 or higher and then bringing the resin into contact with an acidic liquid having a pH of 6 or lower.

18. The method of producing a basic gas deodorizing resin composition according to claim 17, wherein the zirconium phosphate particles are zirconium phosphate particles, obtained by bringing α-zirconium phosphate particles into contact with a basic liquid having a pH of 9 or higher and then further bringing the particles into contact with an acidic liquid having a pH of 6 or lower.

19. A method of producing basic gas deodorizing fibers, the method comprising bringing fibers that include zirconium phosphate particles into contact with a basic liquid having a pH of 9 or higher and then bringing the fibers into contact with an acidic liquid having a pH of 6 or lower.

20. The method of producing basic gas deodorizing fibers according to claim 19, wherein the zirconium phosphate particles are zirconium phosphate particles, obtained by bringing α-zirconium phosphate particles into contact with a basic liquid having a pH of 9 or higher and then further bringing the particles into contact with an acidic liquid having a pH of 6 or lower.

\* \* \* \* \*